(12) United States Patent
Kang et al.

(10) Patent No.: US 11,983,255 B2
(45) Date of Patent: May 14, 2024

(54) MOBILITY USER AUTHENTICATION APPARATUS AND METHOD USING BRAIN WAVE

(71) Applicants: Hyundai Motor Company, Seoul (KR); Kia Motors Corporation, Seoul (KR); Sookmyung Women's University Industry-Academic Cooperation Foundation, Seoul (KR)

(72) Inventors: Jeong Su Kang, Seongnam-si (KR); Suh Yeon Dong, Seoul (KR)

(73) Assignees: Hyundai Motor Company, Seoul (KR); Kia Motors Corporation, Seoul (KR); Sookmyung Women's University Industry-Academic Cooperation Foundation, Seoul (KR)

( * ) Notice: Subject to any disclaimer, the term of this patent is extended or adjusted under 35 U.S.C. 154(b) by 246 days.

(21) Appl. No.: 17/023,586

(22) Filed: Sep. 17, 2020

(65) Prior Publication Data

US 2021/0157886 A1 May 27, 2021

(30) Foreign Application Priority Data

Nov. 26, 2019 (KR) ........................ 10-2019-0153683

(51) Int. Cl.
| | |
|---|---|
| *G06F 3/01* | (2006.01) |
| *A61B 5/377* | (2021.01) |
| *B60W 40/08* | (2012.01) |
| *G06F 21/32* | (2013.01) |

(52) U.S. Cl.
CPC .............. *G06F 21/32* (2013.01); *A61B 5/377* (2021.01); *B60W 40/08* (2013.01); *G06F 3/015* (2013.01); *B60W 2040/0809* (2013.01)

(58) Field of Classification Search
CPC ........ G06F 21/32; G06F 3/015; B60W 40/08; B60W 2040/0809
See application file for complete search history.

(56) References Cited

U.S. PATENT DOCUMENTS

| | | | | |
|---|---|---|---|---|
| 2004/0097824 | A1* | 5/2004 | Kageyama | .......... B60R 16/0231 340/4.1 |
| 2010/0010365 | A1* | 1/2010 | Terao | .................. B60K 28/063 600/544 |
| 2015/0033258 | A1* | 1/2015 | Klappert | ................ A61B 5/398 725/38 |
| 2018/0273053 | A1* | 9/2018 | Ruemelin | .............. B62D 1/286 |

FOREIGN PATENT DOCUMENTS

| | | | | |
|---|---|---|---|---|
| CN | 105899255 | A * | 8/2016 | ......... A61B 5/04001 |
| CN | 106843480 | A * | 6/2017 | ............. G06F 3/015 |
| CN | 108375912 | A * | 8/2018 | ............. G06F 3/015 |

* cited by examiner

*Primary Examiner* — Towfiq Elahi
(74) *Attorney, Agent, or Firm* — Slater Matsil, LLP

(57) ABSTRACT

A mobility user authentication apparatus using a brain wave signal includes a receiver configured to receive a predetermined user input from a passenger of a mobility, a display configured to display a preset image list to the passenger on a predetermined area in the mobility based on the received user input, a sensor configured to collect a brain wave signal for the passenger for a predetermined time, and a controller configured to perform authentication for the passenger by analyzing the collected brain wave signal.

20 Claims, 9 Drawing Sheets

−9.3 μN    −0.6 μN

−1.8 μN    13.0 μN

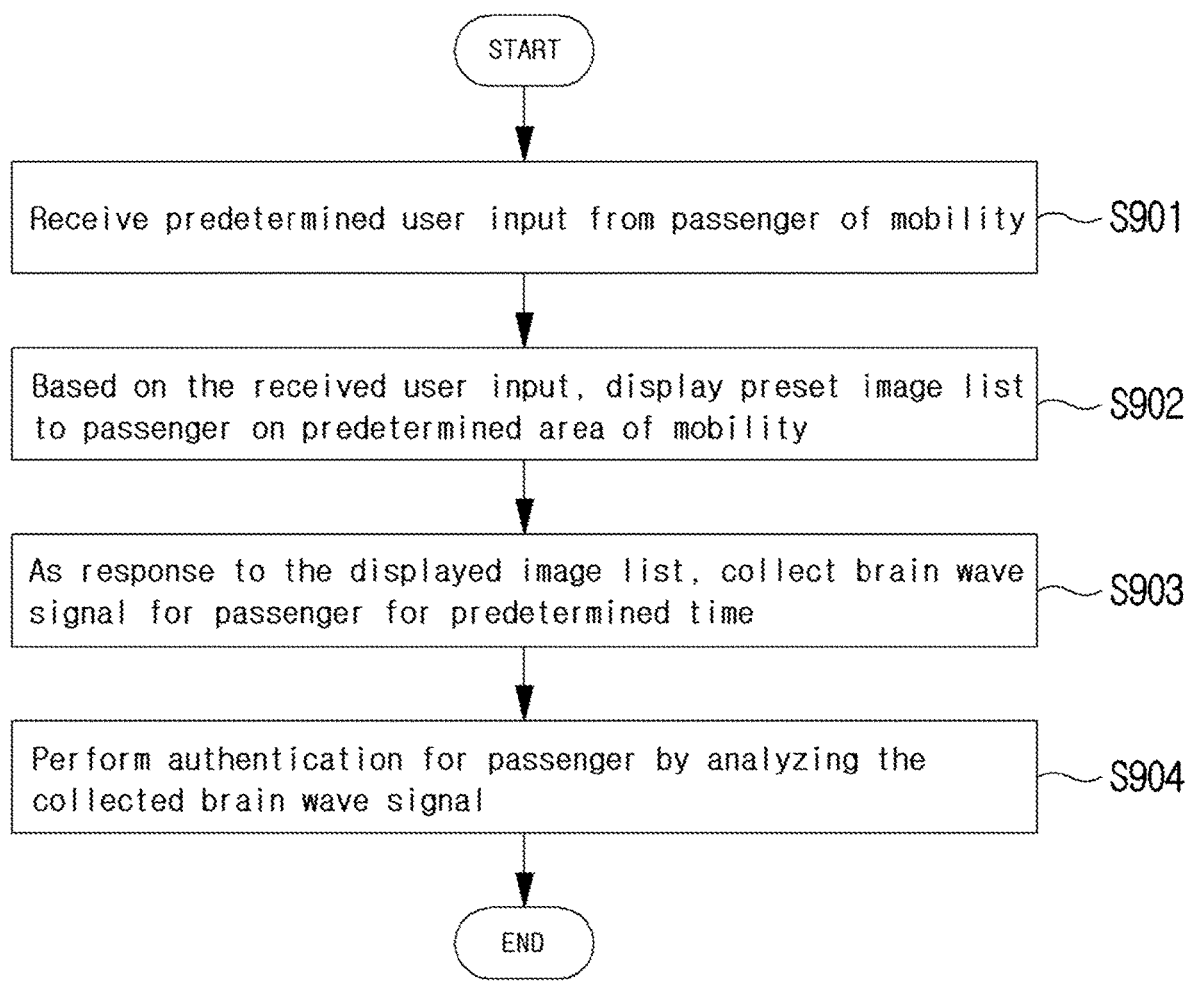

MOBILITY USER AUTHENTICATION APPARATUS AND METHOD USING BRAIN WAVE

CROSS-REFERENCE TO RELATED APPLICATIONS

This application claims the benefit of Korean Patent Application No. 10-2019-0153683, filed on Nov. 26, 2019, which application is hereby incorporated herein by reference.

TECHNICAL FIELD

The present disclosure relates to a mobility controlling method and apparatus.

BACKGROUND

The statements in this section merely provide background information related to the present disclosure and may not constitute prior art.

As one of the transport means, a vehicle (or mobility) is a very important means and tool for living a life in the modern world. Furthermore, a mobility itself may be regarded as something special that gives meaning to someone.

As technology is advanced, functions provided by a mobility also gradually evolve. For example, in recent years, mobilities not only transport a passenger to a destination, but also meet a passenger's needs for faster and safer travel to a destination. In addition, new devices are being added to a mobility system in order to satisfy a passenger's aesthetic taste and comfort. In addition, the existing devices like steering wheels, transmissions and acceleration/deceleration devices are also being developed so that more functions can be provided to users.

Meanwhile, a brain-computer interface or a brain-machine interface is a field of controlling a computer or a machine according to a person's intention by using brain wave signals. ERP (Event-Related Potential) is closely related to cognitive functions.

SUMMARY

The present disclosure relates to a mobility controlling method and apparatus. Particular embodiments relate to a mobility controlling method and apparatus.

An embodiment of the present invention provides an apparatus and method for authenticating a mobility user on the basis of a passenger's brain wave signal.

Another embodiment of the present invention provides an apparatus and method for performing authentication for a passenger by analyzing the passenger's brain wave signal in response to an image displayed on a mobility display.

The embodiments of the present disclosure are not limited to the above-mentioned embodiments, and other embodiments that are not mentioned will be clearly understood by those skilled in the art through the following descriptions.

According to embodiments of the present invention, a mobility user authentication apparatus using a brain wave signal may be provided. The apparatus may include a receiver for receiving a predetermined user input from a passenger of a mobility, a display for displaying a preset image list to the passenger on a predetermined area in the mobility on the basis of the received user input, a sensor for collecting a brain wave signal for the passenger for a predetermined time as a response to the displayed image list, and a controller for performing authentication for the passenger by analyzing the collected brain wave signal.

The passenger may be a person sitting in the driver's seat in the mobility.

The passenger may sit in a first seat in the mobility, and the first seat may be taken by a passenger who may play a leading role in controlling the mobility.

The user input may be a pressure with a predetermined magnitude or above that is applied to at least one of a start button, a brake pedal, a seat, and a steering wheel of the mobility.

The image list may include at least one or more images with different image characteristics.

The image characteristics may include at least one of a chroma, a color depth, brightness, contrast, clarity, mellowness, and content information.

The image list may include an image with a predetermined relevance to the passenger.

The image with a predetermined relevance to the passenger may be an image activating a brain wave signal in the frontal lobe of the passenger or in some areas of the frontal lobe.

The number of images constituting the image list may be set by a user input or be preset in the mobility.

The display may display at least one or more images constituting the image list in a sequential order on a predetermined area of a mobility.

The at least one or more images may be at least some of all the images constituting the image list.

The display may display each of the at least one or more images on the predetermined area for a predetermined time.

The predetermined time may be different for each of the at least one or more images.

The predetermined area may be included in at least one of a display capable of being projected in the mobility, a head up display (HUD), and a navigation display.

The sensor may collect a brain wave signal of the passenger gazing at an image displayed on the predetermined area of the mobility for a predetermined time.

The collected brain wave signal may be a brain wave signal in at least one of a time domain, a frequency domain, and a spatial domain.

The analysis may include determining whether or not the brain wave signal characteristic information collected for the predetermined time is similar to pre-stored brain wave signal characteristic information for each passenger.

The brain wave signal characteristic information of each passenger may be pre-learned brain wave signal characteristic information for each passenger corresponding to each image of the image list.

The determining of similarity may be determined, for at least one image of the image list, on the basis of whether or not the number of results determining that the brain wave signal characteristic information is similar to the pre-stored brain wave signal characteristic for each passenger is equal to or greater than a predetermined value.

The determining of similarity may be determined, for at least one image of the image list, by using a predetermined number of images with a higher priority.

The controller may further include providing the passenger with a result of the authentication for the passenger.

In addition, according to embodiments of the present invention, a mobility user authentication method using a brain wave signal may be provided. The method may include receiving a predetermined user input from a passenger of a mobility, displaying a preset image list to the passenger on a predetermined area in the mobility on the basis of the received user input, as a response to the displayed image list, collecting a brain wave signal for the passenger for a predetermined time, and performing authentication for the passenger by analyzing the collected brain wave signal.

The passenger may be a person sitting in the driver's seat in the mobility.

The passenger may sit in a first seat in the mobility, and the first seat may be taken by a passenger who may play a leading role in controlling the mobility.

The user input may be a pressure with a predetermined magnitude or above that is applied to at least one of a start button, a brake pedal, a seat, and a steering wheel of the mobility.

The image list may consist of at least one or more images with different image characteristics.

The image characteristics may include at least one of a chroma, a color depth, brightness, contrast, clarity, mellowness, and content information.

The image list may include an image with a predetermined relevance to the passenger.

The image with a predetermined relevance to the passenger may be an image activating a brain wave signal in the frontal lobe of the passenger or in some areas of the frontal lobe.

The number of images constituting the image list may be set by a user input or be preset in the mobility.

The displaying on a predetermined area of a mobility may display at least one or more images constituting the image list in a sequential order on the predetermined area of the mobility.

The at least one or more images may be at least some of all the images constituting the image list.

The displaying on a predetermined area of the mobility may display each of the at least one or more images on the predetermined area for a predetermined time.

The predetermined time may be different for each of the at least one or more images.

The predetermined area may be included in at least one of a display capable of being projected in the mobility, a head up display (HUD), and a navigation display.

The collecting for a predetermined time may collect a brain wave signal of the passenger gazing at an image displayed on the predetermined area of the mobility for a predetermined time.

The collected brain wave signal may be a brain wave signal in at least one of a time domain, a frequency domain, and a spatial domain.

The analysis may include determining whether or not the brain wave signal characteristic information collected for the predetermined time is similar to pre-stored brain wave signal characteristic information for each passenger.

The brain wave signal characteristic information of each passenger may be pre-learned brain wave signal characteristic information for each passenger corresponding to each image of the image list.

The determining of similarity may be determined, for at least one image of the image list, on the basis of whether or not the number of results determining that the brain wave signal characteristic information is similar to the pre-stored brain wave signal characteristic for each passenger is equal to or greater than a predetermined value.

The determining of similarity may be determined, for at least one image of the image list, by using a predetermined number of images with a higher priority.

The authenticating for the passenger may further include providing the passenger with a result of the authentication for the passenger.

The features briefly summarized above with respect to embodiments of the present disclosure are merely exemplary aspects of the detailed description below of the present disclosure, and do not limit the scope of the present disclosure.

According to embodiments of the present invention, an apparatus and method for authenticating a mobility user on the basis of a passenger's brain wave signal may be provided.

In addition, according to embodiments of the present invention, an apparatus and method for performing authentication for a passenger by analyzing the passenger's brain wave signal in response to an image displayed on a mobility may be provided.

Effects obtained in embodiments of the present disclosure are not limited to the above-mentioned effects, and other effects not mentioned above may be clearly understood by those skilled in the art from the above description.

BRIEF DESCRIPTION OF THE DRAWINGS

In order that the disclosure may be well understood, there will now be described various forms thereof, given by way of example, reference being made to the accompanying drawings, in which:

FIG. 9 is a flowchart illustrating a method of operating a user authentication apparatus according to one embodiment of the present invention.

DETAILED DESCRIPTION OF ILLUSTRATIVE EMBODIMENTS

Figure 1:
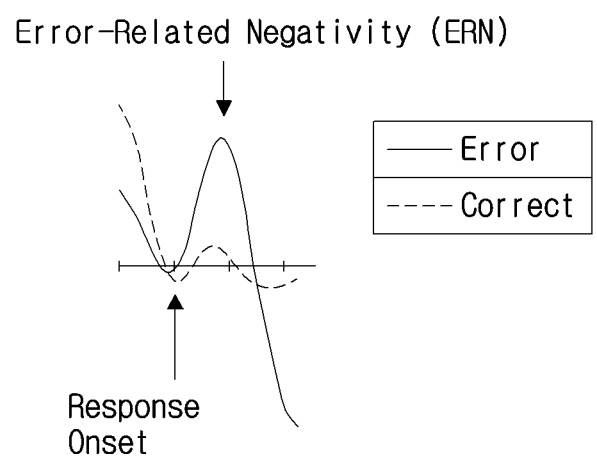
FIG. 1 is a view illustrating a general waveform of ERN in one embodiment of the present disclosure.

The following description is merely exemplary in nature and is not intended to limit the present disclosure, application, or uses. It should be understood that throughout the drawings, corresponding reference numerals indicate like or corresponding parts and features.

The following description is merely exemplary in nature and is not intended to limit the present disclosure, application, or uses. It should be understood that throughout the drawings, corresponding reference numerals indicate like or corresponding parts and features.

Exemplary embodiments of the present disclosure will be described in detail such that the ordinarily skilled in the art would easily understand and implement an apparatus and a method provided by embodiments of the present disclosure in conjunction with the accompanying drawings. However, the present disclosure may be embodied in various forms and the scope of the present disclosure should not be construed as being limited to the exemplary embodiments.

In describing embodiments of the present disclosure, well-known functions or constructions will not be described in detail when they may obscure the spirit of the present disclosure.

In embodiments of the present disclosure, it will be understood that when an element is referred to as being "connected to", "coupled to", or "combined with" another element, it can be directly connected or coupled to or combined with the another element or intervening elements may be present therebetween. It will be further understood that the terms "comprises", "includes", "have", etc. when used in embodiments of the present disclosure specify the presence of stated features, integers, steps, operations, elements, components, and/or combinations thereof but do not preclude the presence or addition of one or more other features, integers, steps, operations, elements, components, and/or combinations thereof.

It will be understood that, although the terms "first", "second", etc. may be used herein to describe various elements, these elements should not be limited by these terms. These terms are only used to distinguish one element from another element and are not used to show order or priority among elements. For instance, a first element discussed below could be termed a second element without departing from the teachings of the present disclosure. Similarly, the second element could also be termed as the first element.

In embodiments of the present disclosure, distinguished elements are termed to clearly describe features of various elements and do not mean that the elements are physically separated from each other. That is, a plurality of distinguished elements may be combined into a single hardware unit or a single software unit, and conversely one element may be implemented by a plurality of hardware units or software units. Accordingly, although not specifically stated, an integrated form of various elements or separated forms of one element may fall within the scope of the present disclosure. Also, the terms, such as 'unit' or 'module', etc., should be understood as a unit that processes at least one function or operation and that may be embodied in a hardware manner (e.g., a processor), a software manner, or a combination of the hardware manner and the software manner.

In embodiments of the present disclosure, all of the constituent elements described in various forms should not be construed as being essential elements but some of the constituent elements may be optional elements. Accordingly, embodiments configured by respective subsets of constituent elements in a certain form also may fall within the scope of the present disclosure. In addition, embodiments configured by adding one or more elements to various elements also may fall within the scope of the present disclosure.

As an electrical activity of neurons constituting a brain, a brain wave signal (or brain signal, brain wave) means a bio signal that directly and indirectly reflects a conscious or nonconscious state of a person. A brain wave signal can be measured in every area of human scalp, and its wavelength has a frequency of mainly 30 Hz or below and a potential difference of scores of microvolts. Depending on brain activity and state, various waveforms may appear. Research on interface control using a brain wave signal according to a person's intention is underway. A brain wave signal may be obtained by using EEG (Electro Encephalo Graphy) using electrical signals caused by brain activities, MEG (Magneto Encephalo Graphy) using magnetic signals occurring with electrical signals, and fMRI (functional Magnetic Resonance Imaging) or fNIRS (functional Near-Infrared Spectroscopy) using a change of oxygen saturation in the blood. Although fMRI and fNIRS are useful techniques for measuring brain activities, fMRI has a low time-resolution and fNIRS has a low spatial-resolution in general. Due to these limitations, EEG signals are mostly used by virtue of excellent portability and time-resolution.

A brain wave signal changes spatially and over time according to brain activity. As a brain wave signal is usually difficult to analyze and its waveform is not easy to visually analyze, various processing methods are proposed.

For example, according to the number of oscillations (frequency), brain wave signals may be classified based on frequency bands (power spectrum classification). The classification considers a measured brain wave signal as a linear sum of simple signals at each specific frequency, decomposes the signal into each frequency component and indicates a corresponding amplitude. A brain wave signal at each frequency may be obtained by using pre-processing normally for noise elimination, the Fourier transform into frequency domain, and a band-pass filter (BPF).

More particularly, according to frequency band, brain waves may be classified into delta, theta, alpha, beta and gamma waves. Delta waves are brain waves with a frequency of 3.5 Hz or below and an amplitude of 20~200 μV, mainly appearing in normal deep sleep or newborns. In addition, delta waves may increase as our awareness of the physical world decreases. Generally, theta waves are brain waves with a frequency of 3.5~7 Hz, mainly appearing in emotionally stable states or in sleep.

In addition, theta waves are generated mainly in the parietal cortex and in the occipital cortex and may appear during calm concentration for recollecting a memory or meditating. Generally, alpha waves are brain waves with a frequency of 8~12 Hz, mainly appearing in relaxed and comfortable states. In addition, alpha waves are normally generated in the occipital cortex during rest and may diminish in sleep. Generally, beta waves are brain waves with a frequency of 13~30 Hz, mainly appearing in a state of tension, which is bearable enough, or while a certain level of attention is paid. In addition, beta waves are mainly generated in the frontal cortex and are related to an awakened state or concentrated brain activities, pathological phenomena and medicinal effects. Beta waves may appear in a wide area throughout the brain. In addition, specifically, the beta waves may be divided into SMR waves with a frequency of 13~15 Hz, mid-beta waves with a frequency of 15~18 Hz and high beta waves with a frequency of 20 Hz and above. As beta waves appear to be stronger under stress like anxiety and tension, they are called stress waves. Gamma waves are brain waves that generally have a frequency of 30~50 Hz, mainly appearing in a strongly excited state or during high-level cognitive information processing. In addition, gamma waves may appear in an awaking state of consciousness and during REM sleep and may also be overlapped with beta waves.

Each of the brain wave signals according to frequency band is associated with a specific cognitive function. For example, delta waves are associated with sleep, theta waves are associated with working memory, and alpha waves are associated with attention or inhibition. Thus, the property of a brain wave signal at each frequency band selectively displays a specific cognitive function. In addition, the brain wave signal at each frequency band may show a little different aspect in each measuring part on the surface of the head. The cerebral cortex may be divided into frontal cortex, parietal cortex, temporal cortex and occipital cortex. These parts may have a few different roles. For example, the occipital cortex corresponding to the back of head has the primary visual cortex and thus can primarily process visual information. The parietal cortex located near the top of head has the somatosensory cortex and thus can process motor/sensory information. In addition, the frontal cortex can process information related to memory and thinking, and the temporal cortex can process information related to auditory sense and olfactory sense.

Meanwhile, for another example, a brain wave signal may be analyzed by using ERP (Event-Related Potential). ERP is an electrical change in a brain in association with a stimulus from outside or a psychological process inside. ERP means a signal including an electrical activity of the brain, which is caused by a stimulus including specific information (for example, image, voice, sound, command of execution, etc.) after a certain time since the stimulus is presented.

To analyze an ERP, a process of separating a signal from a noise is desired. An averaging method may be mainly used. Particularly, by averaging brain waves measured based on stimulus onset time, it is possible to remove brain waves, which are not related to a stimulus, and to pick out only a related potential, that is, a brain activity commonly associated with stimulus processing.

As ERP has a high time resolution, it is closely related to research on cognitive function. ERP is an electrical phenomenon that is evoked by an external stimulus or is related to an internal state. According to types of stimuli, ERPs may be classified into auditory sense-related potentials, sight-related potentials, somatic sense-related potentials and olfactory sense-related potentials. According to properties of stimuli, ERPs may be classified into exogenous ERPs and endogenous ERPs. Exogenous ERPs have a waveform determined by an external stimulus, are related to automatic processing, and mainly appear in the initial phase of being given the stimulus. For example, exogenous ERPs are brainstem potentials. On the other hand, endogenous ERPs are determined by an internal cognitive process or a psychological process or state, irrespective of stimuli, and are related to 'controlled processing'. For example, endogenous ERPs are P300, N400, P600, CNV (Contingent Negative Variation), etc.

Names given to ERP peaks normally include a polarity and a latent period, and the peak of each signal has an individual definition and meaning. For example, the positive potential is P, the negative potential is N, and P00 means a positive peak measured about 300 ms after the onset of a stimulus. In addition, 1, 2, 3 or a, b, c and the like are applied according to the order of appearance. For example, P3 means a third positive potential in waveform after the onset of a stimulus.

Hereinafter, various ERPs will be described.

For example, N100 is related to a response to an unpredictable stimulus.

MMN (Mismatch Negativity) may be generated not only by a focused stimulus but also by a non-focused stimulus. MMN may be used as an indicator for whether or not a sense memory (echoic memory) operates before initial attention. P300, which will be described below, appears in a process of paying attention and making judgment, while MMN is analyzed as a process occurring in the brain before paying attention.

For another example, N200 (or N2) is mainly generated according to visual and auditory stimuli and is related to short-term memory or long-term memory, which are types of memories after attention, along with P300 described below.

For yet another example, P300 (or P3) mainly reflects attention to a stimulus, stimulus cognition, memory search and alleviation of uncertain feeling and is related to a perceptual decision distinguishing stimuli from outside. As the generation of P300 is related to a cognitive function, P300 is generated irrespective of types of presented stimuli. For example, P300 may be generated in auditory stimuli, visual stimuli and somatic stimuli. P300 is widely applied to research on the brain-computer interface.

For yet another example, N400 is related to language processing and is caused when a sentence or an auditory stimulus with a semantic error is presented. In addition, N400 is related to a memory process and may reflect a process of retrieving or searching information from long-term memory.

For yet another example, as an indicator showing reconstruction or recollective process, P600 is related to a process of processing a stimulus more accurately based on information stored in long-term memory.

For yet another example, CNV refers to potentials appearing for 200~300 ms and even for a few seconds in the later phase. It is also called slow potentials (SPs) and is related to expectancy, preparation, mental priming, association, attention and motor activity.

For yet another example, ERN (Error-Related Negativity) or Ne (error negativity) is an event-related potential (ERP) generated by a mistake or an error. It may occur when a subject makes a mistake in a sensorimotor task or a similar task. More particularly, when a subject cognizes a mistake or an error, ERN is generated and its negative peak appears mainly in the frontal and central zones for about 50~150 ms. Especially, it may appear in a situation where a mistake related to motor response is likely to occur, and may also be used to indicate a negative self-judgment.

Hereinafter, the major features of ERN will be described in more detail.

FIG. 1 is a view illustrating a general waveform of ERN according to one embodiment of the present disclosure.

Referring to FIG. 1, negative potential values are depicted above the horizontal axis, and positive potential values are depicted below the horizontal axis. In addition, it can be confirmed that an ERP with a negative peak value is generated within a predetermined time range after a response onset for an arbitrary motion. Herein, the response may mean a case where a mistake or an error is made (Error Response). In addition, the predetermined time range may be about 50~150 ms. Alternatively, the predetermined time range may be about 0~100 ms. Meanwhile, in the case of a correct response, an ERP is generated which has a relatively smaller negative peak than ERN.

As an ERP of initial negativity, ERN is time-locked until a response error occurs. In addition, ERN is known to reflect the reinforcement activity of a dopaminergic system related to behavioral monitoring. ERN includes the fronto-striatal loop including the rostral cingulate zone. Meanwhile, dopamine is associated with the reward system of brain that usually forms a specific behavior and motivates a person thereby providing pleasure and reinforced feelings. When a behavior obtaining an appropriate reward is repeated, it is learned as a habit. In addition, more dopamine is released through emotional learning, and a new behavior is attempted due to the release of dopamine. Thus, reward-driven learning is called reinforcement learning.

In addition, ERN may be generated in 0~100 ms after the onset of an erroneous response that is caused during an interference task (for example, Go-noGo task, Stroop task, Flanker task, and Simon task) through the frontal cortex lead.

In addition, together with CRN described below, ERN is known to reflect a general behavior monitoring system that can distinguish a right behavior and a wrong behavior.

In addition, the fact that ERN reaches a maximum amplitude at the frontal cortex electrode is known to reflect that an intracerebral generator is located in the rostral cingulate zone or the dorsal anterior cingulate cortex (dACC) zone.

In addition, ERN may show a change of amplitude according to a negative emotional state.

In addition, ERN may be reported even in a situation where behavioral monitoring is performed based on external evaluation feedback unlike internal motor expression, and may be classified as FRN described below.

In addition, ERN may be generated not only when having cognized a mistake or an error but also before cognizing the mistake or the error.

In addition, ERN may be generated not only as a response to his/her own mistake or error but also as a response to a mistake or error of others.

In addition, ERN may be generated not only as a response to a mistake or an error but also as a response to anxiety or stress for a predetermined performance task or object.

In addition, as a larger peak value of ERN is obtained, it may be considered as reflecting a more serious mistake or error.

Meanwhile, for yet another example, being an event-related potential (ERP) that is generated after ERN, Pe (Error Positivity) is an ERP with a positive value, which is generated mainly at the frontal cortex electrode in about 150~300 ms after a mistake or an error. Pe is known as a reaction that realizes a mistake or an error and pays more attention. In other words, Pe is related to an indicator of a conscious error information processing process after error detection. ERN and Pe are known as ERPs related to error monitoring.

Hereinafter, the major features of Pe will be described in more detail.

Figure 2:
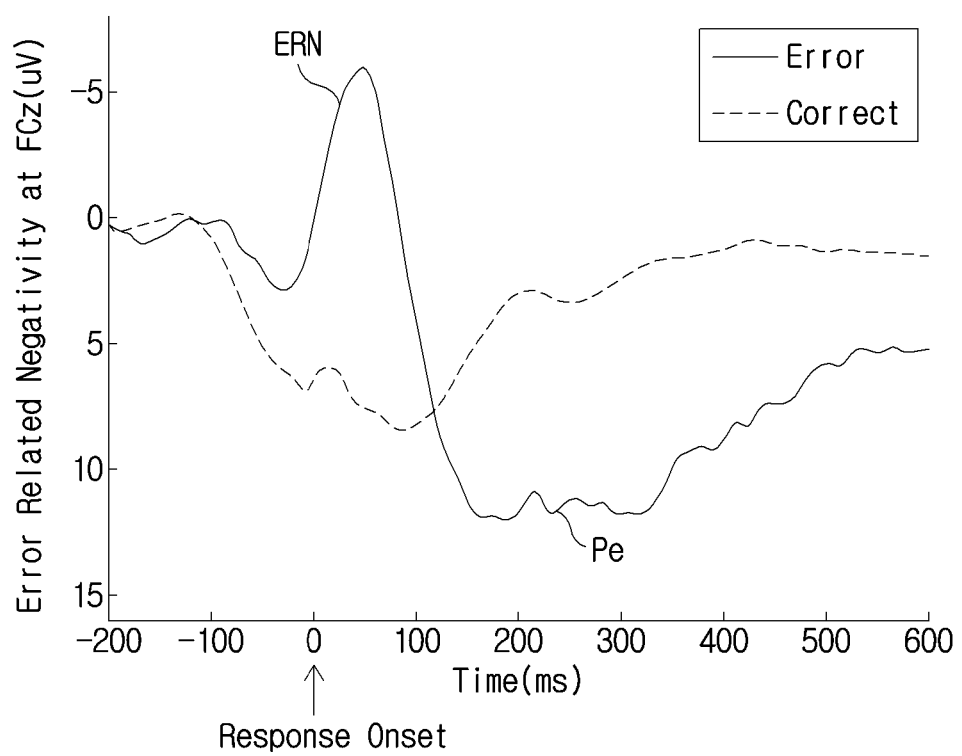
FIG. 2 is a view illustrating general waveforms of ERN and Pe according to one embodiment of the present disclosure.

FIG. 2 is a view illustrating general waveforms of ERN and Pe according to another embodiment of the present disclosure.

Referring to FIG. 2, negative potential values are depicted above positive potential values. In addition, it can be confirmed that an ERP with a negative peak value, that is an ERN, is generated within a first predetermined time range after a response onset for an arbitrary motion. Herein, the response may mean a case where a mistake or an error is made (Error Response). In addition, the first predetermined time range may be about 50~150 ms. Alternatively, the first predetermined time range may be about 0~200 ms.

In addition, it can be confirmed that an ERP with a positive peak value, that is a Pe, is generated within a second predetermined time range after the onset of the ERN. In addition, the second predetermined time range may be about 150~300 ms after an error onset. Alternatively, the second predetermined time range may mean about 200~400 ms.

Figure 3:
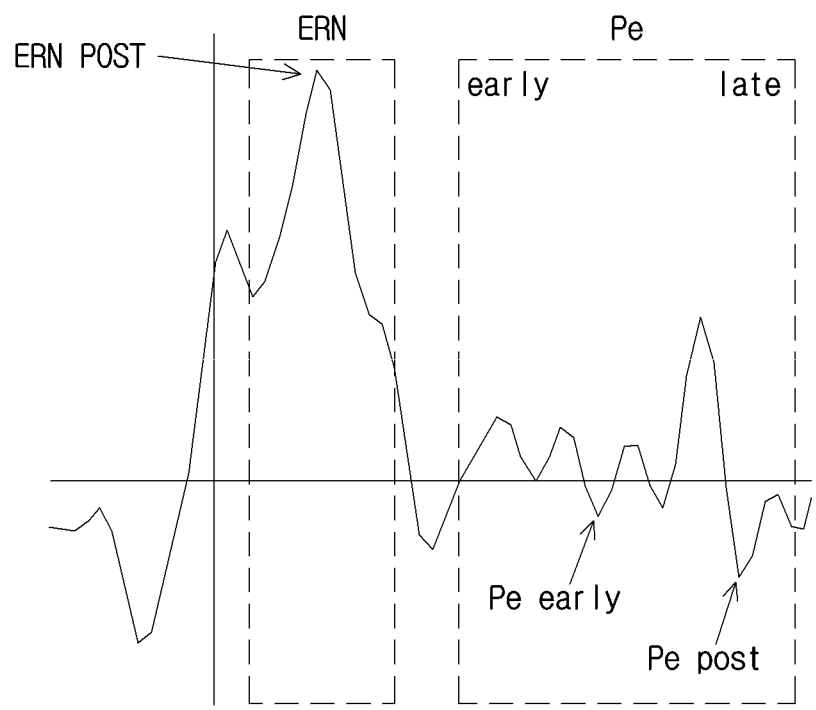
FIG. 3 is a view illustrating a deflection characteristic of Pe according to another embodiment of the present disclosure.

FIG. 3 is a view illustrating a deflection characteristic of Pe in one embodiment of the present disclosure.

Referring to FIG. 3, like P3, Pe has a wide deflection characteristic, and the plexus generator includes not only the areas of posterior cingulate cortex and insula cortex but also more anterior cingulate cortex.

In addition, Pe may reflect an emotional evaluation of an error and an attention to a stimulus like P300. In addition, ERN indicates a conflict between a right response and a wrong response, and Pe is known to be a response that realizes a mistake and pays more attention. In other words, ERN may be generated in a process of detecting a stimulus, and Pe may be generated depending on attention in a process of processing a stimulus. When ERN and/or Pe have relatively large values respectively, it is known that the values are related to an adaptive behavior intended to respond more slowly and more accurately after a mistake.

Figure 4A:
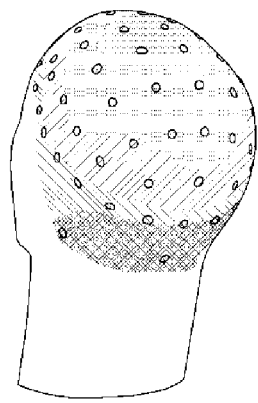
FIGS. 4A and 4B are views respectively illustrating measurement areas of ERP and Pe in one embodiment of the present disclosure.
Figure 4B:
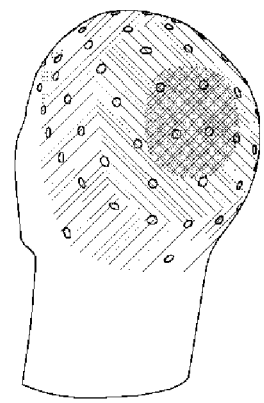

FIGS. 4A and 4B are views illustrating measurement areas of ERP and Pe according to one embodiment of the present disclosure.

ERN and Pe are known as ERPs related to error monitoring. Regarding the measurement areas of ERN and Pe, a largest negative value and a largest positive value may normally be measured in the central area. However, there may be a little difference according to measurement conditions. For example, FIG. 4A is the main area where ERN is measured, and the largest negative value of ERN may normally be measured in the midline frontal or central zone (that is, FCZ). In addition, FIG. 4B is the main area where Pe is measured, and a large positive value of Pe may normally be measured in a posterior midline zone as compared to ERN.

Meanwhile, for yet another example, FRN (Feedback-Related Negativity) is an event-related potential (ERP) that is related to error detection obtained based on external evaluation feedback. ERN and/or Pe detect an error based on an internal monitoring process. However, in the case of FRN, when being obtained based on external evaluation feedback, it may operate similarly to the process of ERN.

In addition, FRN and ERN may share many electrophysiological properties. For example, FRN has a negative peak value at the frontal cortex electrode in about 250~300 ms after the onset of a negative feedback and may be generated in the dorsal anterior cingulate cortex (dACC) zone like ERN.

In addition, like ERN, FRN may reflect an activity of reinforcement learning by a dopaminergic system. In addition, FRN normally has a larger negative value than a positive feedback and may have a larger value for an unforeseen case than for a predictable result.

Figure 5:
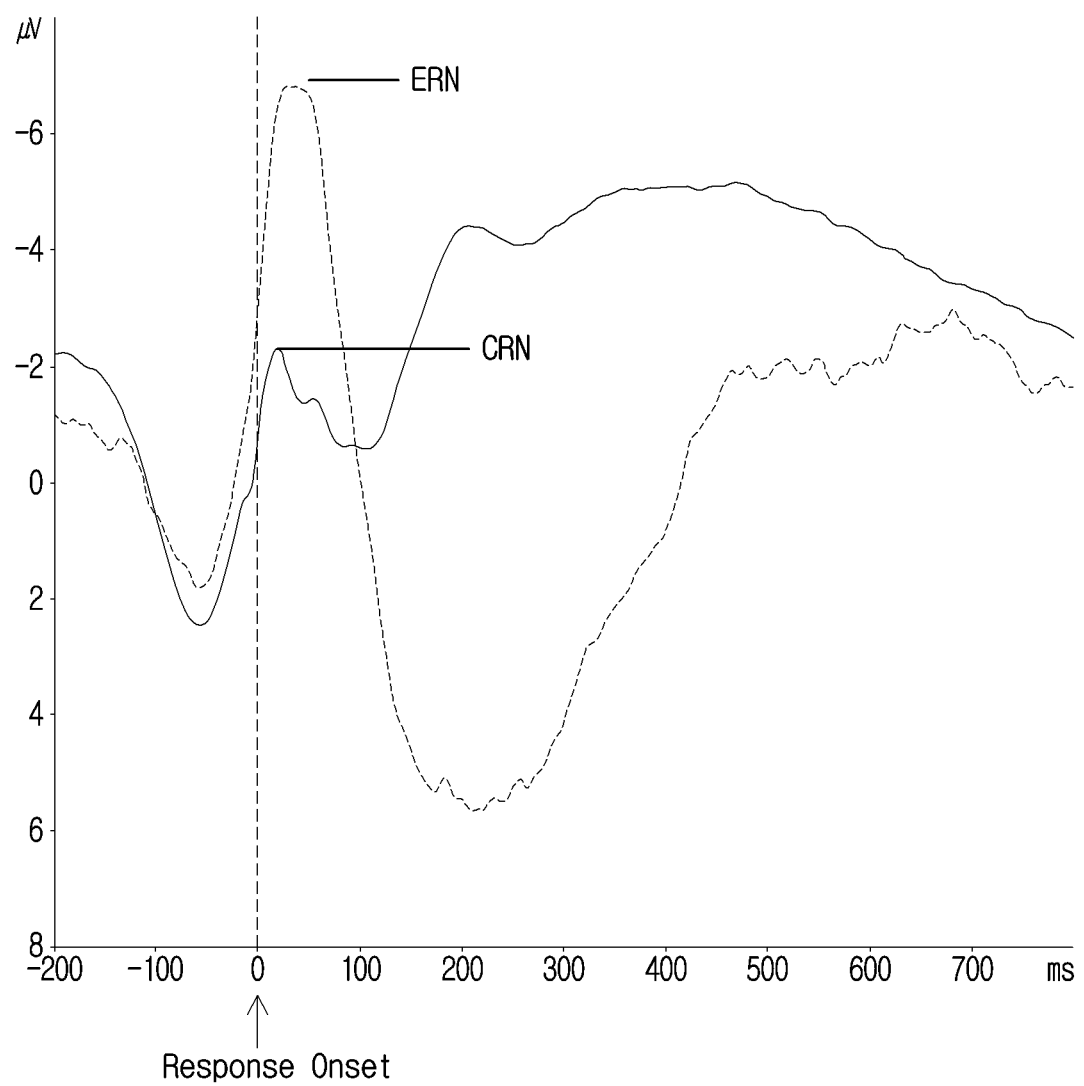
FIG. 5 is a view illustrating general waveforms of ERN and CRN according to one embodiment of the present disclosure.

For yet another example, CRN (Correct-Related Negativity) is an ERP generated by a correct trial and is a negative value that is smaller than ERN. Like ERN, CRN may be generated in the initial latent period (for example, 0~100 ms). FIG. 5 is a view illustrating general waveforms of ERN and CRN in one embodiment of the present disclosure.

For yet another example, Pc (Correct Positivity) is an event-related potential generated following CRN. It is an event-related potential generated in about 150~300 ms after the onset of correct response. The relation between CRN and Pc may be similar to the relation between ERN and Pe.

Meanwhile, ERPs may be classified into stimulus-locked ERPs and response-locked ERPs. The stimulus-locked ERPs and the response-locked ERPs may be divided according to criteria like evoking cause of ERP and response time. For example, an ERP evoked from a moment when a word or a picture is presented to a user from outside may be called a stimulus-locked ERP. In addition, for example, an ERP evoked from a moment when a user speaks or pushes a button may be called a response-locked ERP. Accordingly, based on the above-described criterion, in general, stimulus-locked ERPs are Moo, N200, P2, P3, etc., and response-locked ERPs are ERN, Pe, CRN, Pc, FRN, etc.

Meanwhile, brain waves may be classified according to manifesting motives. Brain waves may be classified into spontaneous brain waves (spontaneous potentials) manifested by a user's will and evoked brain waves (evoked potentials) that are naturally manifested according to external stimuli irrespective of the user's will. Spontaneous brain waves may be manifested when a user moves on his/her own or imagines a movement, while evoked brain waves may be manifested by visual, auditory, olfactory and tactile stimuli, for example.

Meanwhile, brain wave signals may be measured in accordance with the International 10-20 system. The International 10-20 system determines measurement points of brain wave signals on the basis of the relationship between the location of an electrode and the cerebral cortex areas.

Figure 6:
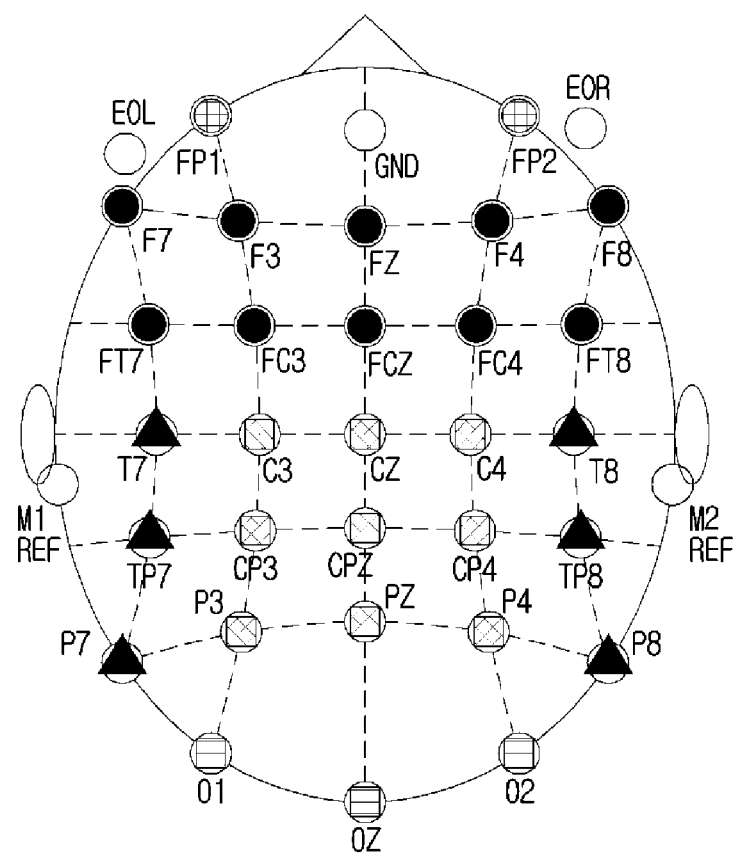
FIG. 6 is a view illustrating EEG measurement channels corresponding to cerebral cortex areas in one embodiment of the present disclosure.

FIG. 6 is a view illustrating EEG measurement channels corresponding to the cerebral cortex areas according to one embodiment of the present disclosure.

Referring to FIG. 6, brain areas (Prefrontal cortex FP1, FP2; Frontal cortex F3, F4, F7, F8, FZ, FC3, FC4, FT7, FT8, FCZ; Parietal cortex C3, C4, CZ, CP3, CP4, CPZ, P3, P4, PZ; Temporal cortex T7, T8, TP7, TP8, P7, P8; Occipital cortex O1, O2, OZ) correspond to 32 brain wave measurement channels. For each of the channels, data may be obtained and analysis may be performed for each cerebral cortex area by using the data.

Figure 7:
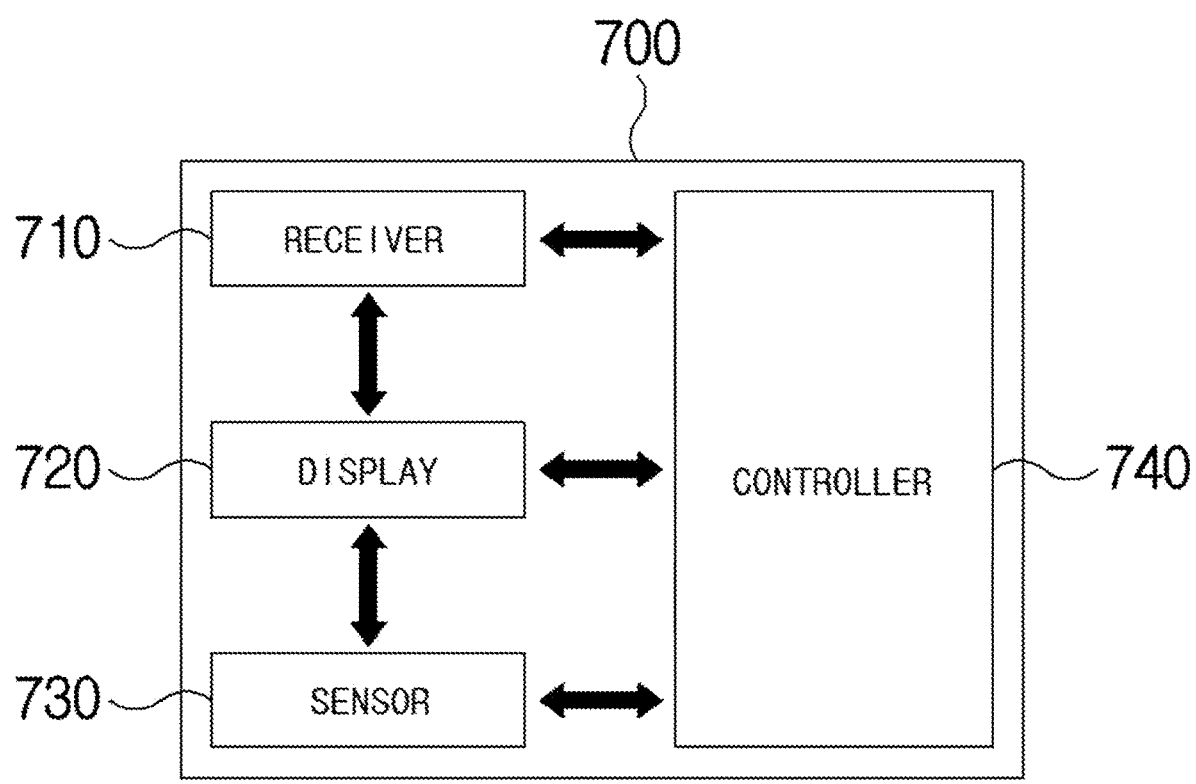
FIG. 7 is a block diagram illustrating a configuration of an apparatus for performing user authentication on the basis of a passenger's brain wave signal according to one embodiment of the present invention.

FIG. 7 is a block diagram illustrating a configuration of an apparatus for performing user authentication on the basis of a passenger's brain wave signal according to one embodiment of the present invention.

In recent years, the emergence of autonomous driving mobilities and an increasing amount of research on the next-generation intelligent transport system (cooperative-intelligent transport system, C-ITS) have highlighted the importance of mobility authentication or driver (or user) authentication or both. Particularly, in the case of driver authentication, since every operation of a mobility is determined by a driver, whether or not the driver is authenticated is an important matter. In addition, driver authentication is necessary to prevent various mobility crimes including a theft in a mobility.

Embodiments of the present disclosure may provide an apparatus and method for authenticating a mobility driver by using a brain wave signal.

As one type of biometric identification, user authentication using a brain wave signal has such features as universality, particularity, convenience of collection, and low possibility of falsification. In other words, there are biometric identification techniques that are not available to those who have a particular disease or illness, while techniques using brain wave signals may use brain waves possessed by anyone (Universality). Also, brain wave signals are unique to each person (Particularity). Also, brain wave signals (especially, EEG) are not difficult to collect (Convenience of collection). Also, brain wave signals are difficult to falsify especially with respect to authentication (Low possibility of falsification).

A mobility user authentication apparatus of embodiments of the present disclosure may provide a passenger with a preset image list in order to perform user authentication. In addition, a mobility user authentication apparatus of the present disclosure may perform a user authentication by analyzing the passenger's brain wave signal that is generated as a response to the provided image list.

Referring to FIG. 7, a mobility user authentication apparatus 700 may include a receiver 710, a display 720, a sensor 730 and/or a controller 740. It should be noted, however, that only some of the components necessary for explaining the present embodiment are shown, and the components included in the mobility user authentication apparatus 700 are not limited to the above-described example. For example, two or more constituent units may be implemented in one constituent unit, and an operation performed in one constituent unit may be divided and executed in two or more constituent units. Also, some of the constituent units may be omitted or additional constituent units may be added.

The mobility user authentication apparatus 700 of embodiments of the present disclosure may receive a predetermined user input from a passenger of a mobility. In addition, the receiver 710 may perform the operation.

Herein, a passenger may mean a person sitting in the driver's seat of a mobility. For example, the passenger may be a driver or a user of a corresponding mobility.

In addition, a user input may be an input for providing start information for a user authentication process regarding the mobility. For example, a user input may be a pressure with a predetermined magnitude or above that is applied to a start button or a brake pedal. Alternatively, a user input may be a pressure with a predetermined magnitude that is applied to a steering handle. Alternatively, a user input may be a pressure with a predetermined magnitude that is applied to a seat in which a passenger sits.

The user input may be different according to each user. In other words, the magnitude of the user input may be different according to each user, and different buttons or devices may be used by each user.

The mobility user authentication apparatus 700 of embodiments of the present disclosure may display a preset image list to a passenger on a predetermined area of the mobility on the basis of the received user input. In addition, the display 720 may perform the operation.

It is known that a brain wave signal (for example, EEG) can show a specific signal pattern for a certain visual stimulus. In other words, EEGs with different features may be output from a user according to characteristics of an image provided to the user.

Herein, the image characteristics may include a chroma, a color depth, brightness, contrast, clarity, mellowness, and a content.

Also, regarding the image characteristics, a channel feature for measuring a brain wave signal may be considered. In other words, as brain wave signals can indicate different aspects in each measurement area of the head surface, the occipital lobe corresponding to the back of head has the primary visual cortex and thus can primarily process visual information, and the parietal lobe located near the top of head has the somatosensory cortex and thus can process motor/sensory information. In addition, the frontal lobe can process information related to memory, high-level thinking and/or emotion, and the temporal lobe can process information related to auditory sense and olfactory sense. Accordingly, a visual image capable of stimulating the occipital lobe, an image that has such a relationship with a user as to stimulate the frontal lobe, or a high-level image may be considered.

For example, a brain wave signal that is generated according to the image characteristics may be a signal that is activated in the occipital lobe processing visual information as a response to a chroma, a color depth, brightness, contrast, clarity, mellowness, and content information respectively. Here, the content information may mean other image characteristic information than a chroma, a color depth, brightness, contrast, clarity, and mellowness.

For example, EEG features obtained from a user gazing at a black-and-white image and a color image may be different.

For another example, EEG features may be different when being obtained from a user gazing at an image with many low-frequency characteristics and an image with many high-frequency characteristics.

For yet another example, EEG features may be different when being from a user gazing at a letter image and a person-shaped image.

For yet another example, EEG features may be different when being obtained from a user gazing at a letter image and a figure image.

For yet another example, EEG features may be different when being obtained from a user gazing at a number image and a Korean character/Roman alphabet image.

In addition, EEG features may be different when being obtained from a user gazing at an image having a predetermined relevance to the user and an image having no relevance to the user.

Herein, an image having a predetermined relevance to a user may mean an image having a personal relationship with the user. For example, it may include a user's photo, a user's family photo, a user's pet photo, a photo of a user's prized possession, and a photo capable of recollecting a user's particular experience. The image having a predetermined relevance to the user may have been already stored by each user.

In addition, the image list may consist of images of which characteristics have relevance to processing functions of each brain area. For example, images may be included which have relevance to processing functions of respective areas like the occipital lobe, the parietal lobe, the frontal lobe, the prefrontal lobe, and the temporal lobe. For example, a brain wave signal that is generated according to an image characteristic having a predetermined relevance to the passenger may be a signal activated as a response to an image having a predetermined relevance to the passenger in the frontal lobe (or a part of the frontal lobe) that processes information associated with memory, high-level thinking and emotions. In other words, the image with a predetermined relevance to the passenger may be an image activating a brain wave signal in the frontal lobe of the passenger or in some areas of the frontal lobe.

Figure 8A:
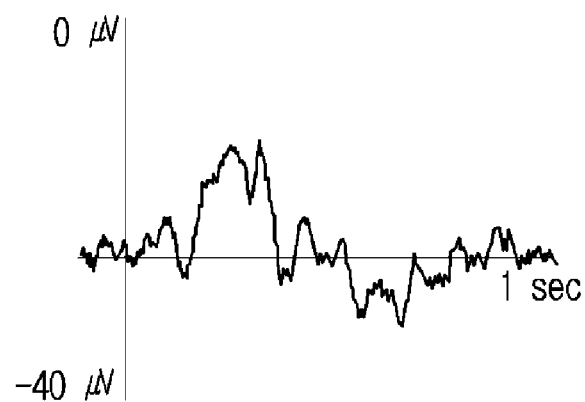
FIGS. 8A and 8B are views illustrating EEG features of a user gazing at images with different characteristics according to one embodiment of the present invention.
Figure 8B:
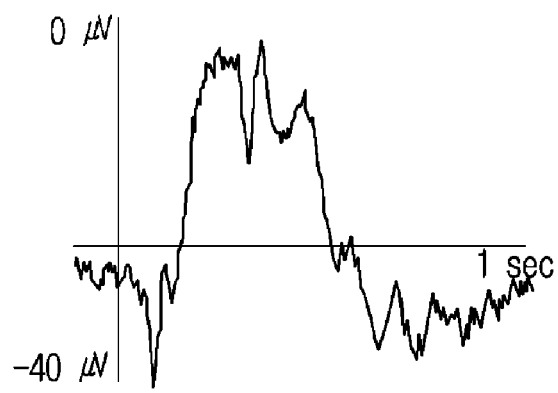

FIGS. 8A and 8B are views illustrating EEG features of a user gazing at images with different characteristics according to one embodiment of the present invention. For example, FIG. 8A and FIG. 8B may be views illustrating EEG features obtained from a user gazing at a black-and-color image and a color image respectively. Alternatively, FIG. 8A and FIG. 8B may be views illustrating EEG features obtained from a user gazing at an image with many low-frequency characteristics and an image with many high-frequency characteristics. Alternatively, FIG. 8A and FIG. 8B may be views illustrating EEG features obtained from a user gazing at an image having a predetermined relevance to the user and an image having no relevance to the user.

Meanwhile, the image list may include at least one or more images with different image characteristics.

For example, an image list may include a black-and-white image, a color image, a letter image, and a user's photo.

For another example, an image list may include a black-and-white image, an image with many low-frequency characteristics, an image with many high-frequency characteristics, a number image, and a photo recollecting a user's particular experience.

The number of images constituting the image list may be set by a user input or be preset in a mobility.

In addition, the mobility user authentication apparatus 700 of embodiments of the present disclosure may display at least one or more images constituting the image list in a sequential order on a predetermined area of a mobility.

Herein, the at least one or more images may be at least some of all the images constituting the image list.

Herein, a sequential order may mean an order of images constituting an image list. For example, when an image list consists of images {A1, . . . , An} (n is an integer greater than 1), a sequential order may mean an order from A1 to An.

The image order may be set by a user input or be preset in a mobility.

Alternatively, an image stored by a user input may be displayed on the predetermined area in preference to other images.

Alternatively, an image having a predetermined relevance to a user may be displayed on the predetermined area in preference to other images.

Herein, each image may be displayed on a predetermined area for a predetermined time. The predetermined time may be different for each image. Alternatively, the predetermined time may be different for each image on the basis of image characteristics.

In addition, each image displayed on a predetermined area may have a predetermined time interval. For example, there may be a time interval of tens of milliseconds to seconds between the image A1 and the image A2. The time interval may be different for each image. Alternatively, the time interval may be different for each image on the basis of image characteristics. No image may be displayed during the time interval. Alternatively, an image with a predetermined color may be displayed during the time interval. A predetermined time interval between images enables a user to remove an afterimage from a previous image.

Here, a predetermined area may be a predetermined area within a display that can be projected in the mobility. The predetermined area may be a predetermined area on a front windshield, a side windshield, a rear windshield, and a projection display that is different from the windshields. The predetermined area may be determined based on at least one of a position of the passenger and a position of the passenger's gaze while the mobility is running.

In addition, a predetermined area may be a predetermined area within a navigation display. Alternatively, it may be a predetermined area on a separate head up display (HUD).

In response to the displayed image list, the mobility user authentication apparatus 700 of the present disclosure may collect a brain wave signal for a passenger for a predetermined time. In addition, the sensor 730 may perform the operation.

Here, the collecting of a brain wave signal for a predetermined time may mean collecting a brain wave signal of a passenger gazing at an image displayed in a predetermined area of a mobility for the predetermined time. The image may be an image constituting an image list.

In addition, the collecting of a brain wave signal for a predetermined time may mean collecting a passenger's brain wave signal for each image that is displayed in a predetermined area of a mobility and is included in an image list.

For example, when an image list consists of images {A1, . . . , An} (n is an integer greater than 1) and the images A1 to An are sequentially displayed in a predetermined area of a mobility, brain wave signal characteristic (or EEG feature) information of a passenger gazing at the images A1 to An may be sequentially collected.

Here, the collected brain wave signal may mean a brain wave signal in at least one of a time domain, a frequency domain, and a spatial domain. Here, the spatial domain may mean a brain wave signal measurement channel.

The mobility user authentication apparatus 700 of embodiments of the present disclosure may perform authentication for a passenger by analyzing the collected brain wave signal. In addition, the controller 740 may perform the operation.

Herein, the analysis may include determining whether or not the brain wave signal characteristic information collected for the predetermined time is similar to pre-stored brain wave signal characteristic information for each passenger.

Herein, brain wave signal characteristic information for each passenger may be a result of prior learning according to passengers. For example, prior learning may be performed for a passenger's brain wave signal characteristic corresponding to each image of an image list. In addition, the brain wave signal characteristic information for each passenger may be updated in real time.

For example, on the basis of similarity determination, the mobility user authentication apparatus 700 of embodiments of the present disclosure may determine whether or not the collected brain wave signal characteristic information is similar to pre-stored brain wave signal characteristic information for each passenger. Herein, the similarity determination may apply various methods of determining similarity such as a technique of extracting a feature point between input images to determine similarity and other conventional techniques used for image recognition or classification.

In addition, when the similarity is determined, a similarity between brain wave signal characteristics may be compared with a predetermined threshold. The predetermined threshold may vary according to an image corresponding to a brain wave signal characteristic. Herein, a similarity between brain wave signal characteristics may be expressed by a probability or a numerical value.

For example, when an image corresponding to a brain wave signal characteristic has a predetermined relevance to a user, a threshold may have a larger value than when an image has no predetermined relevance to the user. For example, when an image corresponding to a brain wave signal characteristic has no predetermined relevance to a user and a threshold is 0.6, for an image that corresponds to a brain wave signal characteristic and has a predetermined relevance to the user, a threshold may be 0.8. In other words, when a similarity of brain wave signal characteristics for an image having a relevance to a user is determined more rigidly, an apparatus capable of more adaptively operating for each user may be provided.

For another example, when an image corresponding to a brain wave signal characteristic is a person-shaped image, a threshold may be larger than when the image is a character image.

In other words, the mobility user authentication apparatus 700 of embodiments of the present disclosure may perform authentication for a passenger by determining whether it is similar or not. In addition, the controller 740 may perform the operation.

Meanwhile, the determining of similarity may include a process of ultimately determining whether or not brain wave signal characteristics are similar by combining determination results for similarity between brain wave signal characteristics for each image included in an image list.

In addition, when brain wave signal characteristics are ultimately determined to be similar, the passenger may be considered to be authenticated.

When an image list consists of images {A1, . . . , An} (n is an integer greater than 1) and the images A1 to An are sequentially displayed in a predetermined area of a mobility, whether or not brain wave signal characteristics are similar may be determined as follows.

For example, when determination results concerning whether or not brain wave signal characteristics are similar for each image may be represented by 0 and 1 and the number of determination results concerning whether or not brain wave signal characteristics are similar for each image among the images A1 to An is equal to or greater than k (k is an integer greater than 1), brain wave signal characteristics may be ultimately determined to be similar. In other words, when the number of determination results that brain wave signal characteristics are similar for each image is equal to or greater than k, brain wave signal characteristics may be ultimately determined to be similar. Herein, when a determination result concerning whether or not they are similar is 0, a similarity between brain wave signal characteristics is below a predetermined threshold. When a determination result concerning whether or not they are similar is 1, a similarity between brain wave signal characteristics is equal to or greater than a predetermined threshold.

For another example, when determination results concerning whether or not brain wave signal characteristics are similar for each image may be represented by 0 and 1 and a result expressed by a weighted sum for the images A1 to An is equal to or greater than m (m is an integer greater than 1), brain wave signal characteristics may be ultimately determined to be similar.

For yet another example, when similarity is determined by using top k (k is an integer greater than 1) images in the descending order of priority among given images, authentication for a passenger may be performed. For example, when brain wave signal characteristics for p or more images (1<=p<=k, p is an integer) among top k images are determined to be similar, the brain wave signal characteristics may be ultimately determined to be similar.

For another example, when brain wave signal characteristics for a predetermined image among the images A1 to An are determined to be not similar, the brain wave signal characteristics may be ultimately determined to be not similar. For example, when a brain wave signal characteristic corresponding to an image having a predetermined relevance to a user is determined to be not similar to a pre-stored brain wave signal characteristic, the brain wave signal characteristics may be ultimately determined to be not similar.

Meanwhile, a condition for performing authentication by determining similarity may be set by a user input.

In addition, the mobility user authentication apparatus 700 may provide a passenger with a result of the authentication.

For example, when authentication fails, a voice prompt notifying the failure of authentication may be provided to a passenger.

For another example, when authentication is successful, a voice prompt notifying the success of authentication may be provided to a passenger or a voice prompt suggesting that a subsequent process following the authentication (for example, button input for starting a mobility) may be provided to a passenger.

For yet another example, a preset voice prompt may be provided to a passenger depending on cases where authentication fails or is successful.

For yet another example, when authentication fails, a passenger may confirm whether or not a re-authentication process is to be performed.

FIG. 9 is a flowchart illustrating a method of operating a user authentication apparatus according to one embodiment of the present invention.

In the step S901, a predetermined user input may be received from a passenger of a mobility.

Here, the passenger may be a person sitting in the driver's seat of the mobility. Alternatively, the passenger may be a person sitting in a first seat in the mobility, and the first seat may mean a seat taken by a passenger who is capable of playing a leading role in controlling the mobility.

Here, the user input may be a pressure with a predetermined magnitude or above that is applied to at least one of a start button, a brake pedal, a seat, and a steering wheel of the mobility.

In the step S902, a preset image list may be displayed to a passenger on a predetermined area of the mobility on the basis of the received user input.

For example, at least one or more images constituting the image list may be displayed in a sequential order on a predetermined area of a mobility. Herein, the at least one or more images may be at least some of all the images constituting the image list.

For another example, each of the at least one or more images may be displayed on the predetermined area for a predetermined time. Here, the predetermined time may be different for each of the at least one or more images.

Here, the predetermined area may be included in at least one of a display capable of being projected in the mobility, a head up display (HUD), and a navigation display.

Here, the image list may consist of at least one or more images with different image characteristics. In addition, the image list may include an image with a predetermined relevance to the passenger. Here, the image with a predetermined relevance to the passenger may be an image activating a brain wave signal in the frontal lobe of the passenger or in some areas of the frontal lobe. In addition, the image list may consist of images of which characteristics have relevance to processing functions of each brain area. For example, images may be included which have relevance to processing functions of respective areas like the occipital lobe, the parietal lobe, the frontal lobe, the prefrontal lobe, and the temporal lobe. For example, a brain wave signal that is generated according to an image characteristic having a predetermined relevance to the passenger may be a signal activated as a response to an image having a predetermined relevance to the passenger in the frontal lobe (or a part of the frontal lobe) that processes information associated with memory, high-level thinking and emotions.

The image characteristics may include at least one of a chroma, a color depth, brightness, contrast, clarity, mellowness, and content information. Here, the content information may mean other image characteristic information than a chroma, a color depth, brightness, contrast, clarity, and mellowness. For example, a brain wave signal that is generated according to the image characteristics may be a signal that is activated in the occipital lobe processing visual information as a response to a chroma, a color depth, brightness, contrast, clarity, mellowness, and content information respectively.

Meanwhile, the number of images constituting the image list may be set by a user input or be preset in the mobility.

In the step S903, as a response to the displayed image list, a brain wave signal for a passenger may be collected for a predetermined time.

For example, a brain wave signal of the passenger gazing at an image displayed on a predetermined area of the mobility may be collected for a predetermined time. Here, the collected brain wave signal may be a brain wave signal in at least one of a time domain, a frequency domain, and a spatial domain.

The step S904 may include performing authentication for a passenger by analyzing the collected brain wave signal.

Herein, the analysis may include determining whether or not the brain wave signal characteristic information collected for the predetermined time is similar to pre-stored brain wave signal characteristic information for each passenger.

The brain wave signal characteristic information for each passenger may be pre-learned brain wave signal characteristic information for each passenger corresponding to each image of the image list.

Meanwhile, the authentication result for the passenger may be provided to the passenger.

Effects obtained in embodiments of the present disclosure are not limited to the above-mentioned effects, and other effects not mentioned above may be clearly understood by those skilled in the art from the foregoing description.

Although exemplary methods of the present disclosure are described as a series of operation steps for clarity of a description, the present disclosure is not limited to the sequence or order of the operation steps described above. The operation steps may be simultaneously performed, or may be performed sequentially but in a different order. In order to implement the method of embodiments of the present disclosure, additional operation steps may be added and/or existing operation steps may be eliminated or substituted.

Various embodiments of the present disclosure are not presented to describe all of the available combinations but are presented to describe only representative combinations. Steps or elements in various embodiments may be separately used or may be used in combination.

In addition, various embodiments of the present disclosure may be embodied in the form of hardware, firmware, software, or a combination thereof. When an embodiment of the present disclosure is embodied in a hardware component, it may be, for example, an application specific integrated circuit (ASIC), a digital signal processor (DSP), a digital signal processing device (DSPD), a programmable logic device (PLD), a field programmable gate array (FPGA), a general processor, a controller, a microcontroller, a microprocessor, etc.

The scope of the present disclosure includes software or machine-executable instructions (for example, operating systems (OS), applications, firmware, programs) that enable methods of various forms to be executed in an apparatus or on a computer, and a non-transitory computer-readable medium storing such software or machine-executable instructions so that the software or instructions can be executed in an apparatus or on a computer.

The description of embodiments of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A mobility user authentication apparatus, the apparatus comprising:
   a receiver configured to receive a predetermined user input from a passenger of a mobility;
   a display configured to display a preset image list to the passenger on a predetermined area in the mobility based on the received user input, wherein the preset image list comprises an image having a predetermined relevance to the passenger and having relevance to processing functions of each brain area, and the predetermined relevance corresponds to a personal characteristic of the passenger;
   a sensor configured to collect a brain wave signal for the passenger for a predetermined time as a response to the preset image list, wherein the brain wave signal for the passenger is a signal activated as a response to the image with the predetermined relevance having the personal characteristic of the passenger and the relevance to the processing functions of each brain area; and
   a controller configured to perform authentication for the passenger by analyzing the collected brain wave signal, wherein the authentication is performed based on a similarity between a collected brain wave signal and a pre-stored brain wave signal for each passenger, the similarity being determined by a comparison with a predetermined threshold that varies according to the image, wherein a value of the predetermined threshold for the image having the predetermined relevance to the passenger is larger than a value of the predetermined threshold for an image having no predetermined relevance to the passenger.

2. The apparatus of claim 1, wherein the predetermined user input is a pressure with a predetermined magnitude or above that is applied to at least one of a start button, a brake pedal, a seat, and a steering wheel of the mobility.

3. The apparatus of claim 1, wherein:
   the preset image list comprises at least one or more images with different image characteristics; and
   the different image characteristics comprise at least one of a chroma, a color depth, brightness, contrast, clarity, mellowness, and content information.

4. The apparatus of claim 1, wherein the image with the predetermined relevance to the passenger is an image activating the brain wave signal in a frontal lobe of the passenger or in some areas of the frontal lobe.

5. The apparatus of claim 1, wherein the display is configured to display at least one or more images of the preset image list in a sequential order on the predetermined area of the mobility.

6. The apparatus of claim 5, wherein the predetermined area comprises an area in at least one of a display capable of being projected in the mobility, a head up display (HUD), and a navigation display.

7. The apparatus of claim 1, wherein the sensor is configured to collect the brain wave signal of the passenger gazing at an image displayed on the predetermined area of the mobility for the predetermined time.

8. The apparatus of claim 1, wherein the controller is configured to perform authentication for the passenger by analyzing the collected brain wave signal by determining whether or not characteristic information of the brain wave signal collected for the predetermined time is similar to pre-stored brain wave signal characteristic information for the passenger.

9. The apparatus of claim 1, wherein the controller is further configured to provide the passenger with a result of the authentication for the passenger.

10. A mobility user authentication method, the method comprising:
   receiving a predetermined user input from a passenger of a mobility;
   based on the received user input, displaying a preset image list to the passenger on a predetermined area in the mobility, wherein the preset image list comprises an image having a predetermined relevance and having relevance to processing functions of each brain area, and the predetermined relevance corresponds to a personal characteristic of the passenger;
   as a response to the preset image list, collecting a brain wave signal for the passenger for a predetermined time, wherein the brain wave signal for the passenger is a signal activated as a response to the image with the predetermined relevance having the personal characteristic of the passenger; and
   performing authentication for the passenger by analyzing the collected brain wave signal, wherein the authentication is performed based on similarity between a collected brain wave signal and a pre-stored brain wave signal for each passenger, and wherein the similarity is determined by a comparison with a predetermined threshold that varies according to the image, wherein a value of the predetermined threshold for the image having the predetermined relevance to the passenger is larger than a value of the predetermined threshold for an image having no predetermined relevance to the passenger.

11. The method of claim 10, wherein the predetermined user input is a pressure with a predetermined magnitude or above that is applied to at least one of a start button, a brake pedal, a seat, and a steering wheel of the mobility.

12. The method of claim 10, wherein:
   the preset image list comprises at least one or more images with different image characteristics; and
   the different image characteristics comprise at least one of a chroma, a color depth, brightness, contrast, clarity, mellowness, and content information.

13. The method of claim 10, wherein the image with the predetermined relevance to the passenger is an image activating the brain wave signal in a frontal lobe of the passenger or in some areas of the frontal lobe.

14. The method of claim 10, wherein displaying on the predetermined area in the mobility comprises displaying at least one or more images of the preset image list in a sequential order on the predetermined area in the mobility.

15. The method of claim 14, wherein the predetermined area comprises an area in at least one of a display capable of being projected in the mobility, a head up display (HUD), and a navigation display.

16. The method of claim 10, wherein collecting the brain wave signal for the passenger for the predetermined time comprises collecting the brain wave signal of the passenger gazing at an image displayed on the predetermined area in the mobility for the predetermined time.

17. The method of claim 10, wherein performing the authentication for the passenger by analyzing the collected brain wave signal comprises determining whether or not characteristic information of the collected brain wave signal is similar to pre-stored brain wave signal characteristic information for the passenger.

18. The method of claim 10, further comprising providing the passenger with a result of the authentication for the passenger.

19. A mobility user authentication apparatus, the apparatus comprising:
a receiver configured to receive a predetermined user input from a passenger of a mobility;
a display configured to display a preset image list to the passenger on a predetermined area in the mobility based on the received user input, wherein the preset image list comprises an image having a predetermined relevance to the passenger and having relevance to processing functions of each brain area, wherein the predetermined relevance corresponds to a personal characteristic of the passenger, and wherein the preset image list comprises a plurality images with different image characteristics selected from the group consisting of chroma, color depth, brightness, contrast, clarity, mellowness, and content information;
a sensor configured to collect a brain wave signal for the passenger for a predetermined time as a response to the preset image list, wherein the brain wave signal for the passenger is a signal activated as a response to the image with the predetermined relevance having the personal characteristic of the passenger and the relevance to the processing functions of each brain area; and
a controller configured to perform authentication for the passenger by analyzing the collected brain wave signal, wherein the authentication is performed based on similarity between a collected brain wave signal and a pre-stored brain wave signal for each passenger, the similarity being determined by a comparison with a predetermined threshold that varies according to the image, wherein a value of the predetermined threshold for the image having the predetermined relevance to the passenger is larger than a value of the predetermined threshold for an image having no predetermined relevance to the passenger.

20. The apparatus of claim 19, wherein the predetermined user input is a pressure with a predetermined magnitude or above that is applied to a start button, a brake pedal, a seat, or a steering wheel of the mobility.

* * * * *